United States Patent
DiCarlo et al.

(10) Patent No.: US 9,339,591 B2
(45) Date of Patent: *May 17, 2016

(54) EMBOLIZATION

(71) Applicant: Boston Scientific Scimed Inc., Maple Grove, MN (US)

(72) Inventors: Paul DiCarlo, Middleboro, MA (US); Thomas V. Casey, II, Grafton, MA (US); Stephan P. Mangin, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/897,998

(22) Filed: May 20, 2013

(65) Prior Publication Data

US 2015/0157768 A1    Jun. 11, 2015

Related U.S. Application Data

(63) Continuation of application No. 13/491,915, filed on Jun. 8, 2012, now Pat. No. 8,445,022, which is a continuation of application No. 12/769,172, filed on Apr. 28, 2010, now Pat. No. 8,216,612, which is a continuation of application No. 10/791,552, filed on Mar. 2, 2004, now Pat. No. 7,736,671.

(51) Int. Cl.
| | |
|---|---|
| *A61K 9/14* | (2006.01) |
| *A61L 31/04* | (2006.01) |
| *A61B 17/12* | (2006.01) |
| *A61K 9/00* | (2006.01) |
| *A61K 9/16* | (2006.01) |
| *A61L 24/00* | (2006.01) |
| *A61L 24/04* | (2006.01) |
| *A61L 31/14* | (2006.01) |
| *A61B 17/42* | (2006.01) |

(52) U.S. Cl.
CPC ............ *A61L 31/04* (2013.01); *A61B 17/12022* (2013.01); *A61B 17/12031* (2013.01); *A61B 17/12036* (2013.01); *A61B 17/12186* (2013.01); *A61K 9/0019* (2013.01); *A61K 9/167* (2013.01); *A61L 24/0015* (2013.01); *A61L 24/0036* (2013.01); *A61L 24/046* (2013.01); *A61L 31/14* (2013.01); *A61B 17/42* (2013.01); *A61B 2017/1205* (2013.01); *A61L 2300/62* (2013.01); *Y10T 428/2982* (2015.01); *Y10T 428/2998* (2015.01)

(58) Field of Classification Search
None
See application file for complete search history.

(56) References Cited

U.S. PATENT DOCUMENTS

| | | | | |
|---|---|---|---|---|
| 6,846,896 | B2 * | 1/2005 | Yamaguchi | .......... C08G 65/336 525/478 |
| 7,736,671 | B2 * | 6/2010 | DiCarlo | .......... A61B 17/12022 424/489 |
| 8,216,612 | B2 * | 7/2012 | DiCarlo | .......... A61B 17/12022 424/489 |
| 8,445,022 | B2 * | 5/2013 | DiCarlo | .......... A61B 17/12022 424/489 |
| 2003/0235794 | A1 * | 12/2003 | Yoshioka | ........... G03C 1/49845 430/566 |

FOREIGN PATENT DOCUMENTS

| | | | |
|---|---|---|---|
| JP | 08339132 | * | 12/1996 |
| JP | 2000310832 | * | 11/2000 |
| JP | 2001201815 | * | 7/2001 |
| JP | 2004020593 | * | 1/2004 |
| MC | 200043 | * | 7/2002 |

OTHER PUBLICATIONS

Grayaa et al., Synthesis of Highly fluorinated Nonionic Surfactacnts, J. of Dispersion Science and Technology, 2003, 24(6), 749-753. ABS.*

* cited by examiner

*Primary Examiner* — Alton Pryor
(74) *Attorney, Agent, or Firm* — Kacvinsky Daisak Bluni PLLC

(57) ABSTRACT

Embolization, as well as related particles, compositions, and methods, are disclosed.

33 Claims, 5 Drawing Sheets

EMBOLIZATION

CROSS REFERENCE TO RELATED APPLICATIONS

This application is a continuation of U.S. application Ser. No. 13/491,915, filed on Jun. 8, 2012, now U.S. Pat. No. 8,445,022, which is a continuation of U.S. application Ser. No. 12/769,172, filed on Apr. 28, 2010, which is a continuation of U.S. application Ser. No. 10/791,552, filed on Mar. 2, 2004, now U.S. Pat. No. 7,736,671, which are hereby incorporated by reference in their entirety.

TECHNICAL FIELD

The invention relates to embolization, as well as related particles, compositions, and methods.

BACKGROUND

Therapeutic vascular occlusions (embolizations) are used to prevent or treat pathological conditions in situ. Compositions including embolic particles are used for occluding vessels in a variety of medical applications. Delivery of embolic particles through a catheter is dependent on size uniformity, density and compressibility of the embolic particles.

SUMMARY

In one aspect, the invention features a particle that includes a first polymer and that has a diameter of from about ten microns to about 3,000 microns. The particle has an interior region and a surface region, and the surface region of the particle has a higher weight percent of the first polymer than the interior region.

In another aspect, the invention features a composition that includes particles in a carrier fluid. At least some of the particles have a diameter of from about ten microns to about 3,000 microns. At least some of the particles that have a diameter of from about ten microns to about 3,000 microns include a first polymer and have an interior region and a surface region, the interior region having a lower weight percent of the first polymer than the surface region.

In a further aspect, the invention features a method of manufacturing embolic particles. The method includes forming a mixture that contains a first polymer and a gelling compound. The method also includes treating the mixture to form a particle with a diameter of from about ten microns to about 3,000 microns. The particle has an interior region and a surface region, and the interior region has a lower weight percent of the first polymer than the surface region.

In another aspect, the invention features a method that includes administering to a patient a therapeutically effective amount of embolic particles. The embolic particles have a diameter of from about ten microns to about 3,000 microns and include a first polymer. The embolic particles also have an interior region and a surface region, and the interior region has a lower weight percent of the first polymer than the surface region.

Embodiments may also include one or more of the following.

The interior region can be substantially devoid of the first polymer.

The interior region can include at most about 50 weight percent (e.g., at most about ten weight percent) of the first polymer, and/or at least about 0.1 weight percent (e.g., at least about one weight percent) of the first polymer.

The surface region can include at least about 0.1 weight percent (e.g., at least about 25 weight percent) of the first polymer, and/or at most about 100 weight percent (e.g., at most about 75 weight percent) of the first polymer.

The difference between the weight percent of the first polymer in the interior region and the weight percent of the first polymer at the surface region can be at least about 30 weight percent (e.g., at least about 40 weight percent).

The particle can include from about 0.1 weight percent to about 90 weight percent (e.g., from about ten weight percent to about 80 weight percent, from about 25 weight percent to about 85 weight percent, from about 0.25 weight percent to about 50 weight percent, from about 15 weight percent to about 35 weight percent) of the first polymer.

The particle can have a diameter of at least about 100 microns (e.g., at least about 500 microns; at least about 1,000 microns; at least about 1,500 microns; at least about 2,000 microns), and/or at most about 2,500 microns (e.g., at most about 2,000 microns; at most about 1,500 microns; at most about 1,200 microns; at most about 1,000 microns; at most about 500 microns). The particle can have a diameter of from about 100 microns to about 500 microns or a diameter of from about 500 microns to about 1,200 microns.

The particles can have an arithmetic mean diameter of about 3,000 microns or less and/or about ten microns or more.

The first polymer can have the formula D-B-[O-(A-O)$_n$-B]$_m$-D, in which O is a first oligomeric segment, B is a first coupling segment, A is a second coupling segment, D is a polyfluoro oligomeric group, m is from one to 20 (e.g., from one to ten), and n is from zero to 20 (e.g., from two to ten).

O can be a polyurethane, a polyurea, a polyamide, a polyalkylene oxide, a polycarbonate, a polyester, a polylactone, a polysilicone, a polyethersulfone, a polyolefin, a polyvinyl, a polypeptide polysaccharide, or an ether and amine linked segment thereof.

A can be a diamine, a diisocyanate, a disulfonic acid, a dicarboxylic acid, a diacid chloride, or a dialdehyde.

B can be a diamine, a diisocyanate, a disulfonic acid, a dicarboxylic acid, a diacid chloride, or a dialdehyde. B can include a functional group (e.g., an ester, a carboxylic acid salt, a sulfonic acid salt, a phosphonic acid salt, a thiol, a vinyl, a secondary amine).

D can be $CF_3(CF_2)_pCH_2CH_2$—, in which p is from two to 20.

D can be $CF_3(CF_2)_m(CH_2CH_{20})_q$—, in which q is from one to ten and m is from one to 20.

D can be $C_8F_{17}CH_2CH_2$—.

The first polymer can be a halogenated polymer (e.g., a fluorinated polymer).

The first polymer can have a backbone and side groups that are more polar than the backbone.

The first polymer can have a molecular weight of from about 500 to about 15,000.

The first polymer can be substantially linear.

The particle can include a second polymer.

The particle can include a polysaccharide (e.g., alginate).

The particle can be substantially spherical.

The particle can have a coating over its surface region. The coating can be bioabsorbable. The coating can be a polymer. The coating can be a polysaccharide, a polysaccharide derivative, or an inorganic ionic salt. The coating can include a therapeutic agent.

The interior region of the particle can have a density of large pores and the surface region of the particle can have a density of large pores. The density of large pores of the interior region can be greater than the density of large pores at the surface region.

The particle can include a therapeutic agent. The therapeutic agent can be bound to the first polymer. The therapeutic agent can be disposed within the pores of the interior region.

The particle can include a ferromagnetic material, a material that is visible by magnetic resonance imaging (an MRI-visible material), and/or a radiopaque material.

The carrier fluid can be a saline solution.

The carrier fluid can be a contrast agent.

The carrier fluid can include a surfactant. For example, the carrier fluid can include from about 0.05 percent by weight to about one percent by weight (e.g., about 0.1 percent by weight, about 0.5 percent by weight) of the surfactant.

The gelling compound can be a polysaccharide (e.g., alginate).

The mixture can include a second polymer.

The second polymer can be a polyvinyl alcohol, a polyacrylic acid, a polymethacrylic acid, a poly vinyl sulfonate, a carboxymethyl cellulose, a hydroxyethyl cellulose, a substituted cellulose, a polyacrylamide, a polyethylene glycol, a polyamide, a polyurea, a polyurethane, a polyester, a polyether, a polystyrene, a polysaccharide, a polylactic acid, a polyethylene, a polymethylmethacrylate, a polycaprolactone, a polyglycolic acid, a poly(lactic-co-glycolic) acid, or a combination thereof.

The method can include forming drops of the mixture, contacting the drops with a gelling agent, reacting the second polymer, and/or removing the gelling compound.

The method can include combining the particles with a pharmaceutically acceptable medium.

The method can include bonding a therapeutic agent to the first polymer.

The method of administration can be by percutaneous injection.

The method of administration can be by a catheter.

The method can include releasing a therapeutic agent from the first polymer.

Embodiments can include one or more of the following advantages.

In some embodiments, a particle with a surface preferential material can be tailored or designed to release a therapeutic agent at a desired time and/or location. For example, such a particle can be used to deliver a therapeutic agent in a relatively rapid manner and/or to a targeted site (e.g., during an embolization procedure).

In certain embodiments, a sustained, controlled-dosage release of an agent (e.g., a therapeutic agent) can be effected by an agent-containing particle that includes a surface preferential material (e.g., to which the agent is bound).

In some embodiments, a burst release of an agent (e.g., a therapeutic agent) can be effected by an agent-containing particle that includes a surface preferential material by, for example, loading the surface preferential material with agent.

In certain embodiments, a combination sustained, controlled-dosage release and burst release of agent (e.g., therapeutic agent) can be obtained with an agent-containing particle that includes a surface preferential material by, for example, coating the surface of the particle with agent and loading the surface preferential material and/or the interior region of the particle with agent. In certain embodiments, the agent that is coated on the surface can first be released in a controlled manner, followed by a burst release of the agent that is loaded in the surface preferential material and/or in the interior region of the particle.

In embodiments, loading the agent onto and/or into the surface preferential material of the particle can target (e.g., physically target) the agent to a desired site (e.g., a site having a condition to be treated, such as a site having a cancer condition). This can allow for a more efficient use of agent. For example, targeted delivery can permit a lower dosage of agent to be used (e.g., thereby reducing side effects due to the agent).

Features and advantages are in the description, drawings, and claims.

DETAILED DESCRIPTION

Figure 1:
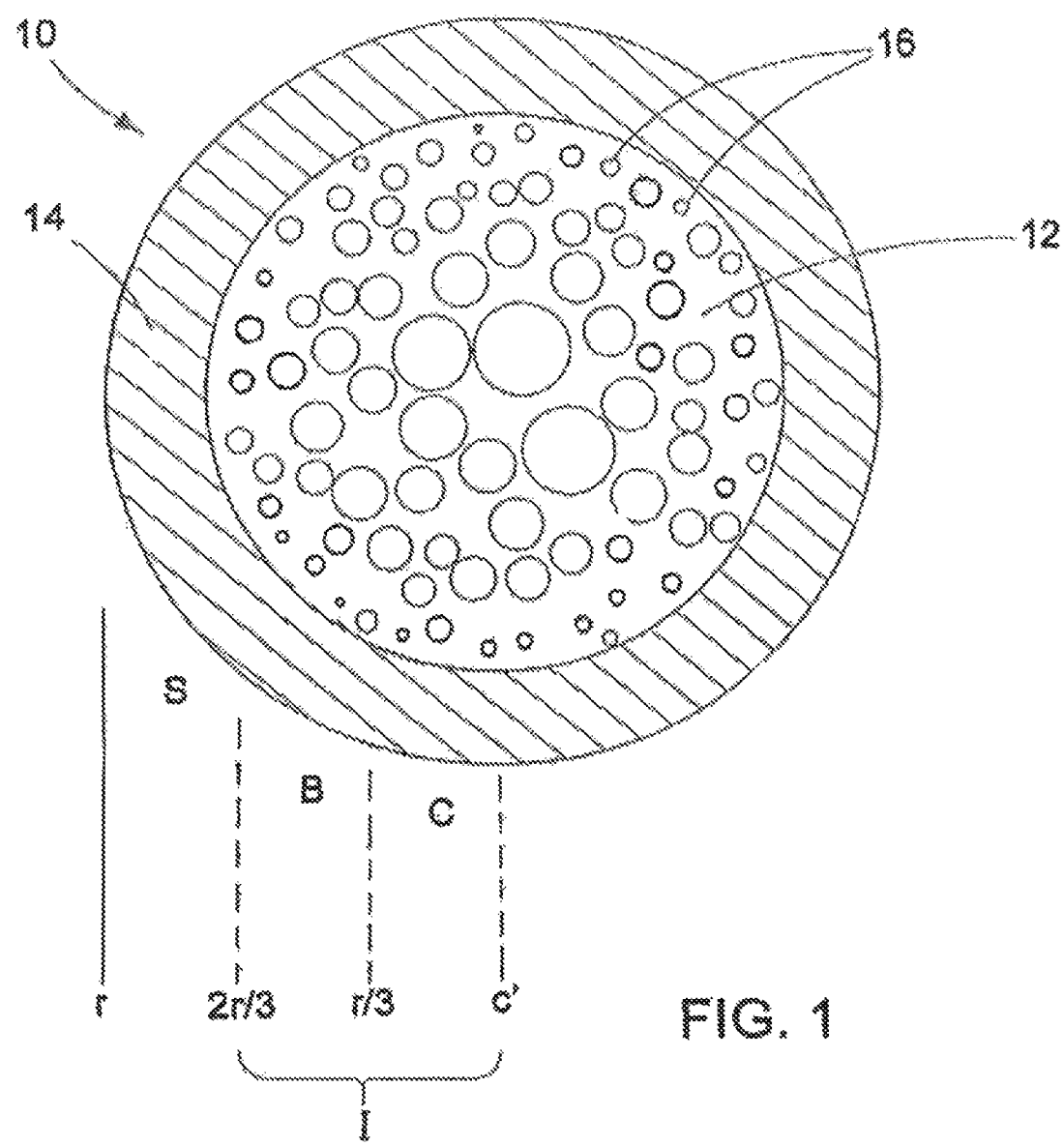
FIG. 1 is a cross-sectional view of an embodiment of a particle.

FIG. 1 shows a substantially spherical particle 10 that includes a matrix material 12 (e.g., a polyvinyl alcohol), a surface preferential material 14 (e.g., a fluorinated polymer), and pores 16. Surface preferential material 14 has one or more therapeutic agents (e.g., drugs) bonded thereto.

Particle 10 can be considered to include a center region, C, from the center c' of particle 10 to a radius of about r/3, a body region, B, from about r/3 to about 2 r/3, and a surface region, S, from about 2r/3 to r. Particle 10 can also be considered to include an interior region, I, from the center c' of particle 10 to a radius of about 2r/3. Region I represents the sum of regions B and C.

In general, the amount of surface preferential material 14 at region S is greater than the amount of surface preferential material 14 in region I. In some embodiments, region I is substantially devoid of surface preferential material 14.

The difference between the weight percent of surface preferential material 14 at region S and the weight percent of surface preferential material 14 in region I can be at least about 30 weight percent (e.g., at least about 35 weight percent, at least about 40 weight percent, at least about 45 weight percent, at least about 50 weight percent, at least about 55 weight percent, at least about 60 weight percent, at least about 65 weight percent, at least about 70 weight percent, at least about 75 weight percent, at least about 80 weight percent, at least about 85 weight percent, at least about 90 weight percent, at least about 95 weight percent), and/or at most about 100 weight percent (e.g., at most about 95 weight percent, at most about 90 weight percent, at most about 85 weight percent, at most about 80 weight percent, at most about 75 weight percent, at most about 70 weight percent, at most about 65 weight percent, at most about 60 weight percent, at most about 55 weight percent, at most about 50 weight percent, at most about 45 weight percent, at most about 40 weight percent, at most about 35 weight percent).

In general, region S can include from about 0.1 weight percent to about 100 weight percent (e.g., from about 20 weight percent to about 100 weight percent, from about 25 weight percent to about 75 weight percent, from about 30 weight percent to about 75 weight percent) of surface preferential material 14. In some embodiments, region S can include at least about 0.1 weight percent (e.g., at least about 0.2 weight percent, at least about 0.5 weight percent, at least about 0.7 weight percent, at least about one weight percent, at least about five weight percent, at least about ten weight percent, at least about 15 weight percent, at least about 20 weight percent, at least about 25 weight percent, at least about 30 weight percent, at least about 35 weight percent, at least about 40 weight percent, at least about 45 weight percent, at least about 50 weight percent, at least about 55 weight percent, at least about 60 weight percent, at least about 65 weight percent, at least about 70 weight percent, at least about 75 weight percent, at least about 80 weight percent, at least about 85 weight percent, at least about 90 weight percent, at least about 95 weight percent, at least about 99 weight percent), and/or at most about 100 weight percent (e.g., at most about 99 weight percent, at most about 95 weight percent, at most about 90 weight percent, at most about 85 weight percent, at most about 80 weight percent, at most about 75 weight percent, at most about 70 weight percent, at most about 65 weight percent, at most about 60 weight percent, at most about 55 weight percent, at most about 50 weight percent, at most about 45 weight percent, at most about 40 weight percent, at most about 35 weight percent, at most about 30 weight percent, at most about 25 weight percent, at most about 20 weight percent, at most about 15 weight percent, at most about ten weight percent, at most about five weight percent, at most about one weight percent, at most about 0.7 weight percent, at most about 0.5 weight percent, at most about 0.2 weight percent), of surface preferential material 14.

Region I generally can include a lower weight percent of surface preferential material 14 than region S. For example, region I can include from about 0.1 weight percent to about 50 weight percent of surface preferential material 14. In some embodiments, region I can include at most about 50 weight percent (e.g., at most about 45 weight percent, at most about 40 weight percent, at most about 35 weight percent, at most about 30 weight percent, at most about 25 weight percent, at most about 20 weight percent, at most about 15 weight percent, at most about ten weight percent, at most about five weight percent, at most about three weight percent, at most about two weight percent, at most about one weight percent, at most about 0.5 weight percent, at most about 0.2 weight percent), and/or at least about 0.1 weight percent (e.g., at least about 0.2 weight percent, at least about 0.5 weight percent, at least about one weight percent, at least about two weight percent, at least about three weight percent, at least about five weight percent, at least about ten weight percent, at least about 15 weight percent, at least about 20 weight percent, at least about 25 weight percent, at least about 30 weight percent, at least about 35 weight percent, at least about 40 weight percent, at least about 45 weight percent), of surface preferential material 14. In some embodiments, region I can be substantially devoid of surface preferential material 14. In certain embodiments, region I may not include any surface preferential material 14.

In general, the amount of surface preferential material 14 in particle 10 can be varied as desired. In some embodiments, particle 10 can include at least about 0.1 weight percent (e.g., at least about 0.2 weight percent, at least about 0.5 weight percent, at least about one weight percent, at least about five weight percent, at least about ten weight percent, at least about 15 weight percent, at least about 20 weight percent, at least about 25 weight percent, at least about 30 weight percent, at least about 35 weight percent, at least about 40 weight percent, at least about 45 weight percent, at least about 50 weight percent, at least about 55 weight percent, at least about 60 weight percent, at least about 65 weight percent, at least about 70 weight percent, at least about 75 weight percent, at least about 80 weight percent, at least about 85 weight percent), and/or at most about 90 weight percent (e.g., at most about 85 weight percent, at most about 80 weight percent, at most about 75 weight percent, at most about 70 weight percent, at most about 65 weight percent, at most about 60 weight percent, at most about 55 weight percent, at most about 50 weight percent, at most about 45 weight percent, at most about 40 weight percent, at most about 35 weight percent, at most about 30 weight percent, at most about 25 weight percent, at most about 20 weight percent, at most about 15 weight percent, at most about ten weight percent, at most about five weight percent, at most about one weight percent, at most about 0.5 weight percent, at most about 0.2 weight percent), of surface preferential material 14. In certain embodiments, particle 10 can include from about 0.1 weight percent to about 90 weight percent (e.g., from about 0.1 weight percent to about 80 weight percent, from about ten weight percent to about 80 weight percent, from about 25 weight percent to about 85 weight percent, from about 0.1 weight percent to about 60 weight percent, from about 0.25 weight percent to about 50 weight percent, from about five weight percent to about 50 weight percent, from about 15 weight percent to about 35 weight percent, from about 0.25 weight percent to about 20 weight percent, from about 0.25 weight percent to about ten weight percent, from about one weight percent to about ten weight percent) of surface preferential material 14. In some embodiments (e.g., when particle 10 includes from about 0.25 weight percent to about 20 weight percent of surface preferential material 14), region S can include from about 25 weight percent to about 70 weight percent of surface preferential material 14. In certain embodiments (e.g., when particle 10 includes from about one weight percent to about ten weight percent of surface preferential material 14), region S can include from about 30 weight percent to about 50 weight percent of surface preferential material 14.

In general, the amount of matrix material 12 in region S is substantially less than the amount of matrix material 12 in region I.

Generally, region I can include from about 30 weight percent to about 100 weight percent of matrix material 12. In some embodiments, region I can include at least about 30 weight percent (e.g., at least about 35 weight percent, at least about 40 weight percent, at least about 45 weight percent, at least about 50 weight percent, at least about 55 weight percent, at least about 60 weight percent, at least about 65 weight percent, at least about 70 weight percent, at least about 75 weight percent, at least about 80 weight percent, at least about 85 weight percent, at least about 90 weight percent, at least about 95 weight percent), and/or at most about 100 weight percent (e.g., at most about 95 weight percent, at most about 90 weight percent, at most about 85 weight percent, at most about 80 weight percent, at most about 75 weight percent, at most about 70 weight percent, at most about 65 weight percent, at most about 60 weight percent, at most about 55 weight percent, at most about 50 weight percent, at most about 45 weight percent, at most about 40 weight percent, at most about 35 weight percent), of matrix material 12. In some embodiments (e.g., when particle 10 includes from about ten weight percent to about 97 weight percent of matrix material 12, when particle 10 includes from about ten weight percent to about 90 weight percent of matrix material 12), region I can include from about 30 weight percent to about 100 weight percent of matrix material 12. In certain embodiments (e.g., when particle 10 includes from about ten weight percent to about 90 weight percent of matrix material 12, when particle 10 includes from about 40 weight percent to about 97 weight percent of matrix material 12), region I can include from about 60 weight percent to about 100 weight percent of matrix material 12.

In some embodiments, region S can include matrix material 12, in addition to including surface preferential material 14. For example, region S can include from about 0.1 weight percent to about 75 weight percent (e.g., from about 0.1 weight percent to about 50 weight percent) of matrix material 12. In certain embodiments, region S can include at most about 75 weight percent (e.g., at most about 70 weight percent, at most about 65 weight percent, at most about 60 weight percent, at most about 55 weight percent, at most about 50 weight percent, at most about 45 weight percent, at most about 40 weight percent, at most about 35 weight percent, at most about 30 weight percent, at most about 25 weight percent, at most about 20 weight percent, at most about 15 weight percent, at most about ten weight percent, at most about five weight percent, at most about one weight percent, at most about 0.5 weight percent, at most about 0.2 weight percent), and/or at least about 0.1 weight percent (e.g., at least about 0.2 weight percent, at least about 0.5 weight percent, at least about one weight percent, at least about five weight percent, at least about ten weight percent, at least about 15 weight percent, at least about 20 weight percent, at least about 25 weight percent, at least about 30 weight percent, at least about 35 weight percent, at least about 40 weight percent, at least about 45 weight percent, at least about 50 weight percent, at least about 55 weight percent, at least about 60 weight percent, at least about 65 weight percent, at least about 70 weight percent), of matrix material 12. In some embodiments, region S can be substantially devoid of matrix material 12. In certain embodiments, region S may not include any matrix material 12.

In general, the amount of matrix material 12 in particle 10 can be varied as desired. Particle 10 can include from about ten weight percent to about 100 weight percent (e.g., from about 40 weight percent to about 100 weight percent) of matrix material 12. In some embodiments, particle 10 can include at most about 100 weight percent (e.g., at most about 99 weight percent, at most about 97 weight percent, at most about 95 weight percent, at most about 90 weight percent, at most about 80 weight percent, at most about 70 weight percent, at most about 60 weight percent, at most about 50 weight percent, at most about 40 weight percent, at most about 30 weight percent, at most about 20 weight percent), and/or at least about ten weight percent (e.g., at least about 20 weight percent, at least about 30 weight percent, at least about 40 weight percent, at least about 50 weight percent, at least about 60 weight percent, at least about 70 weight percent, at least about 80 weight percent, at least about 90 weight percent, at least about 95 weight percent, at least about 97 weight percent, at least about 99 weight percent), of matrix material 12.

Matrix material 12 can be formed of one or more polymers (e.g., biocompatible polymers). Examples of polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polyolefins, polypropylenes, polymethylmethacrylates, polycaprolactones, polyglycolic acids, poly(lactic-co-glycolic) acids (e.g., poly(d-lactic-co-glycolic) acids), polysulfones, polyethersulfones, polycarbonates, nylons, silicones, linear or crosslinked polysilicones, and copolymers or mixtures thereof. In some embodiments, matrix material 12 can be substantially formed of a highly water insoluble, high molecular weight polymer. An example of such a polymer is a high molecular weight polyvinyl alcohol (PVA) that has been acetalized. Matrix material 12 can be substantially pure intrachain 1,3-acetalized PVA and substantially free of animal derived residue such as collagen. In some embodiments, particle 10 includes a minor amount (e.g., about 2.5 weight percent or less, about one weight percent or less, about 0.2 weight percent or less) of a gelling material (e.g., a polysaccharide, such as alginate). In certain embodiments, the majority (e.g., at least about 75 weight percent, at least about 90 weight percent, at least about 95 weight percent) of matrix material 12 is a bioabsorbable polymer (e.g., polysaccharide, such as alginate). Matrix material 12 can include, for example, polyvinyl alcohol, alginate, or both polyvinyl alcohol and alginate.

In some embodiments, the type of matrix material 12 used in particle 10 affects the weight percent of surface preferential material 14 at region S of particle 10. For example, if matrix material 12 is a polystyrene, a silicone, a polyurethane, a polypropylene, a polysulfone, or a nylon, then the weight percent of surface preferential material 14 at region S of particle 10 can be relatively high (e.g., 80 weight percent). The weight percent of surface preferential material 14 at region S can be relatively high in such embodiments because, for example, surface preferential material 14 may migrate relatively easily to region S when added to particle 10 during or after the formation of particle 10. However, in some embodiments, if matrix material 12 is, for example, a polymer that is loaded with a radiopaque material, then the weight percent of the same surface preferential material 14 at region S of particle 10 can be relatively low (e.g., 30 weight percent). The weight percent of surface preferential material 14 at region S can be relatively low in such embodiments because, for example, the surface preferential material may be more restricted in its migration toward region S when added to particle 10 during or after the formation of particle 10. Properties of matrix material 12 that can affect the degree of migration of surface preferential material 14 to region S of particle 10 can include density and/or viscosity.

The characteristics of a particle (such as the amount and/or type of materials present at the particle surface) that includes matrix material 12 and surface preferential material 14 can be determined using, for example, one or more of the analytical services (e.g., Proton NMR) provided by Jordi FLP (Bellingham, Mass.).

Surface preferential material 14 can be, for example, a polymer (e.g., a biocompatible polymer). In some embodiments, the polymer can have the following general formula:

$$\text{D-B-[O-(A-O)}_n\text{-B]}_m\text{-D} \qquad (1)$$

In formula (1), [O-(A-O)$_n$-B]$_m$ is a central portion, O is a first oligomeric segment, A is a second coupling segment that links one O to another O within the central portion, D is a polyfluoro oligomeric group, and B is a first coupling segment that links the central portion to D. Generally, n is from zero to 20 (e.g., from two to ten), and m is from one to 20 (e.g., from one to ten). A therapeutic agent can be bound to one or both of the B components of the above surface preferential material.

In general, first oligomeric segment O is a relatively short length of a repeating unit or units. For example, O can have less than about 20 monomeric units and a molecular weight of less than 5000. In some embodiments, O can be a polyurethane, a polyurea, a polyamide, a polyalkylene oxide, a polycarbonate, a polyester, a polylactone, a polysilicone, a polyethersulfone, a polyolefin, a polyvinyl, a polypeptide polysaccharide, or an ether and amine linked segment thereof.

Second coupling segment A is a molecule that is capable of covalently coupling O units together and of forming the second coupling segments within the central portion. Typically, A can have a molecular weight ranging from 40 to 700 and can have difunctionality to permit coupling of two O units. In some embodiments, A can be a diamine, a diisocyanate, a disulfonic acid, a dicarboxylic acid, a diacid chloride, or a dialdehyde. Terminal hydroxyls, amines or carboxylic acids on the O molecules can react with diamines to form O-amides; can react with diisocyanates to form O-urethanes, O-ureas, O-amides; can react with disulfonic acids to form O-sulfonates, O-sulfonamides; can react with dicarboxylic acids to form O-esters, O-amides; can react with diacid chlorides to form O-esters, O-amides; and can react with dialdehydes to form O-acetal, O-imines.

First coupling segment B is a molecule that can provide primary functional groups capable of covalently coupling with the O/A central portion and D components. Additionally, B has secondary functional chemistry for coupling, e.g., therapeutic agents, such as drugs or bioactive components. Typically, B can have a molecular weight ranging from about 40 to about 700. In some embodiments, B can be a functionalized diamine, a functionalized diisocyanate, a functionalized disulfonic acid, a functionalized dicarboxylic acid, a functionalized diacid chloride or a functionalized dialdehyde, in which the functionalized component has secondary functional chemistry that is accessed for chemical attachment of, for example, therapeutic agents. Such secondary groups can be, for example, esters, carboxylic acid salts, sulfonic acid salts, phosphonic acid salts, thiols, vinyls, or secondary amines. Again, terminal hydroxyls, amines or carboxylic acids on the O/A intermediates can react with diamines to form O-amides; can react with diisocyanates to form O-urethanes, O-ureas, O-amides; can react with disulfonic acids to form O-sulfonates, O-sulfonamides; can react with dicarboxylic acids to form O-esters, O-amides; can react with diacid chlorides to form O-esters, O-amides; and can react with dialdehydes to form O-acetal, O-imines.

In some embodiments, D can be a radical of the general formula $CF_3(CF_2)_pCH_2CH_2$— in which p is from two to 20. In certain embodiments, D can have the general formula $CF_3(CF_2)_m(CH_2CH_{20})_q$—in which q is from one to ten and m is from one to 20. In certain embodiments, D is the perfluoroalkyl group $C_8F_{17}CH_2CH_2$—.

Without wishing to be bound by theory, it is believed that a surface preferential material that has formula (1) tends to migrate to the surface of matrix material 12 when added to matrix material 12. In some embodiments, it is believed that the oligomeric fluorine tails of such a surface preferential material can (e.g., when they are immiscible with matrix material 12) help to carry the surface preferential material to the surface of matrix material 12. If a therapeutic agent is bound to the surface preferential material (e.g., to the B components of the surface preferential material), then the therapeutic agent can migrate to the surface of matrix material 12 along with the surface preferential material.

Further examples of surface preferential materials 14 are polymers that include lysine diisocyanate, a fraction of BA-L™ (a fluoroalcohol available from DuPont), and one of the following: polycarbonate diol; polyethylene tetramethylene oxide; polydimethylsiloxane-bis(3-aminopropyl) terminated; trimethyl-1,6-diisocyanatohexane/dihydroxy diphenylsulfone; polyethylene-butylene copolymer diol; 1,6-hexamethylene diisocyanate/polyethylene tetramethylene oxide/polypropylene oxide diol; or amine-terminated oligo-phenylalanine. Another example of surface preferential material 14 is a polymer that includes segmented polyurethane/DABs, polyethylene tetramethylene oxide, and a fraction of BA-L™.

In some embodiments, surface preferential material 14 is a polymer that includes segmented polyurethane/DABs, polyethylene tetramethylene oxide, and a fraction of BA-L™.

Although surface preferential material 14 has been described as being a polymer, in some embodiments, surface preferential material 14 is a non-polymeric material.

In certain embodiments, surface preferential material 14 can be a material that makes particle 10 relatively lubricious and thereby improves the deliverability of particle 10 (e.g., by decreasing the friction between particle 10 and a device used to deliver particle 10).

In certain embodiments, surface preferential material 14 can be bioerodible, such that surface preferential material 14 can eventually break down in the body and either be dispersed throughout the body or excreted from the body.

Surface preferential material 14 can have a molecular weight that is at least about 500 (e.g., at least about 1,000; at least about 2,000; at least about 3,000; at least about 4,000; at least about 5,000; at least about 6,000; at least about 7,000; at least about 8,000; at least about 9,000; at least about 10,000; at least about 11,000; at least about 12,000; at least about 13,000; at least about 14,000), and/or at most about 15,000 (e.g., at most about 14,000; at most about 13,000; at most about 12,000; at most about 11,000; at most about 10,000; at most about 9,000; at most about 8,000; at most about 7,000; at most about 6,000; at most about 5,000; at most about 4,000; at most about 3,000; at most about 2,000; at most about 1,000). The molecular weight of a polymer can be measured by, for example, gel permeation chromatography.

Surface preferential materials are described, for example, in Santerre, U.S. Published Patent Application No. US 2003/0097120 A1, which is incorporated herein by reference.

As noted above, surface preferential material 14 of particle 10 is bound to one or more therapeutic agents (e.g., drugs). Surface preferential material 14 can be selected or designed to release the therapeutic agent over a period of time, and/or to release the agent when triggered by certain factors (e.g., exposure to the bloodstream, temperature, pH, light).

Therapeutic agents include agents that are negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); cells (of human origin, from an animal source, or genetically engineered); stem cells; immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); anti-inflammatory agents; calcium entry blockers; antineoplastic/antiproliferative/anti-mitotic agents (e.g., paclitaxel, doxorubicin, cisplatin); antimicrobials; anesthetic agents; anti-coagulants; vascular cell growth promoters; vascular cell growth inhibitors; cholesterol-lowering agents; vasodilating agents; agents which interfere with endogenous vasoactive mechanisms; and survival genes which protect against cell death. Therapeutic agents are described, for example, in co-pending U.S. patent application Ser. No. 10/615,276, filed on Jul. 8, 2003, and entitled "Agent Delivery Particle", which is incorporated herein by reference.

In some embodiments, other regions of particle 10 can include a therapeutic agent. For example, region I of particle 10 can include a therapeutic agent. In certain embodiments, pores 16 of particle 10 can include a therapeutic agent.

In general, particle 10 can have a diameter of from about ten microns to about 3,000 microns. In some embodiments, particle 10 can have a diameter of about 3,000 microns or less (e.g., about 2,500 microns or less; about 2,000 microns or less; about 1,500 microns or less; about 1,200 microns or less; about 1,000 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,000 microns or more; about 1,200 microns or more; about 1,500 microns or more; about 2,000 microns or more; about 2,500 microns or more).

In certain embodiments, the diameter of particle 10 can be from about 100 microns to about 700 microns; from about 500 microns to about 700 microns; from about 100 microns to about 500 microns; from about 100 microns to about 300 microns; from about 300 microns to about 500 microns; from about 500 microns to about 1,200 microns; from about 500 microns to about 700 microns; from about 700 microns to about 900 microns; from about 900 microns to about 1,200 microns.

Regions C, B, and S can be characterized by the relative size of pores 16 present in particle 10 in each region, the density of pores 16 (the number of pores 16 per unit volume of particle 10) in each region, and/or the mass density (the density of matrix material 12 and surface preferential material 14 mass per unit volume of particle 10) in each region.

In general, the mean size of pores 16 in region C of particle 10 is greater than the mean size of pores 16 at region S of particle 10. In some embodiments, the mean size of pores 16 in region C of particle 10 is greater than the mean size of pores 16 in region B particle 10, and/or the mean size of pores 16 in region B of particle 10 is greater than the mean size of pores 16 at region S particle 10. In some embodiments, the mean size of pores 16 in region C is about 20 microns or more (e.g., about 30 microns or more, from about 20 microns to about 35 microns). In certain embodiments, the mean size of pores 16 in region B is about 18 microns or less (e.g. about 15 microns or less, from about 18 microns to about two microns). In some embodiments, the mean size of pores 16 at region S is about one micron or less (e.g. from about 0.1 micron to about 0.01 micron). In certain embodiments, the mean size of pores 16 in region B is from about 50 percent to about 70 percent of the mean size of pores 16 in region C, and/or the mean size of pores 16 at region S is about ten percent or less (e.g., about two percent or less) of the mean size of pores 16 in region B. In some embodiments, the surface of particle 10 and/or its region S is/are substantially free of pores having a diameter greater than about one micron (e.g., greater than about ten microns). In certain embodiments, the mean size of pores 16 in the region from 0.8r to r (e.g., from 0.9r to r) is about one micron or less (e.g., about 0.5 micron or less, about 0.1 micron or less). In some embodiments, pores 16 in the region from the center of particle 10 to 0.9r (e.g., from the center of particle 10 to 0.8r) are about ten microns or greater and/or have a mean size of from about two microns to about 35 microns. In certain embodiments, the mean size of pores 16 in the region from 0.8r to r (e.g., from 0.9r to r) is about five percent or less (e.g., about one percent or less, about 0.3 percent or less) of the mean size of pores 16 in the region from the center to 0.9r. In some embodiments, the largest pores in particle 10 can have a size in the range of about one percent or more (e.g., about five percent or more, about ten percent or more) of the diameter of particle 10. The size of pores 16 in particle 10 can be measured by viewing a cross-section of particle 10. For irregularly shaped (nonspherical) pores, the maximum visible cross-section is used.

Generally, the density of pores 16 in region C of particle 10 is greater than the density of pores 16 at region S of particle 10. In some embodiments, the density of pores 16 in region C of particle 10 is greater than the density of pores 16 in region B of particle 10, and/or the density of pores 16 in region B of particle 10 is greater than the density of pores 16 at region S of particle 10.

In general, the mass density in region C of particle 10 is less than the mass density at region S of particle 10. In some embodiments, the mass density in region C of particle 10 is less than the mass density in region B of particle 10, and/or the mass density in region B of particle 10 is less than the mass density at region S of particle 10.

In general, the density of particle 10 (e.g., as measured in grams of material per unit volume) is such that it can be readily suspended in a carrier fluid (e.g., a pharmaceutically acceptable carrier, such as a saline solution, a contrast solution, or a mixture thereof) and remain suspended during delivery. In some embodiments, the density of particle 10 is from about 1.1 grams per cubic centimeter to about 1.4 grams per cubic centimeter. As an example, for suspension in a saline-contrast solution, the density of particle 10 can be from about 1.2 grams per cubic centimeter to about 1.3 grams per cubic centimeter.

In certain embodiments the region of small pores near the surface of particle 10 can be relatively stiff and incompressible, which can enhance resistance to shear forces and abrasion. In addition, the variable pore size profile can produce a symmetric compressibility and, it is believed, a compressibility profile. As a result, particle 10 can be relatively easily compressed from a maximum, at rest diameter to a smaller, compressed first diameter. Compression to an even smaller diameter, however, may involve substantially greater force. Without wishing to be bound by theory, it is believed that a variable compressibility profile can be the result of a relatively weak, collapsible inter-pore wall structure in the center region of particle 10 (where the pores are relatively large), and a stiffer inter-pore wall structure near the surface of particle 10 (where the pores are more numerous and relatively small). It is further believed that a variable pore size profile can enhance elastic recovery after compression. It is also believed that the pore structure can influence the density of particle 10 and the rate of carrier fluid or body fluid uptake.

In some embodiments, a plurality of the particles (e.g., in an embolic composition) can be delivered through a catheter having a lumen with a cross-sectional area that is smaller (e.g., about 50 percent or less) than the uncompressed cross-sectional area of the particles. In such embodiments, the particles are compressed to pass through the catheter for delivery into the body. Typically, the compression force is provided indirectly, by depressing the syringe plunger to increase the pressure applied to the carrier fluid. In general, the particles are relatively easily compressed to diameters sufficient for delivery through the catheter into the body. The relatively robust, rigid surface region of the particles can resist abrasion when the particles contact hard surfaces such as syringe surfaces, hard plastic or metal stopcock surfaces, and/or the catheter lumen wall (made of, e.g., Teflon) during delivery. Once in the body, the particles can substantially recover to original diameter and shape for efficient transport in the carrier and body fluid stream. At the point of occlusion, the particles can again compress as they aggregate in the occlusion region. The particles can form a relatively dense occluding mass. The compression of the particles in the body is generally determined by the force provided by body fluid flow in the lumen. In some embodiments, the compression may be limited by the compression profile of the particles, and the number of particles needed to occlude a given diameter may be reduced.

In certain embodiments, the sphericity of particle 10 after compression in a catheter (e.g., after compression to about 50 percent or more of the cross-sectional area of particle 10) is about 0.8 or more (e.g., about 0.85 or more, about 0.9 or more, about 0.95 or more, about 0.97 or more). Particle 10 can be, for example, manually compressed, essentially flattened, while wet to about 50 percent or less of its original diameter and then, upon exposure to fluid, regain a sphericity of about 0.8 or more (e.g., about 0.85 or more, about 0.9 or more, about 0.95 or more, about 0.97 or more). The sphericity of a particle can be determined using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures 15 particles in an image in the form of a fiber, rod or sphere. The sphericity of a particle, which is computed as Da/Dp (where $Da=\sqrt{(4A/\pi)}$; $Dp=P/\pi$; A=pixel area; P=pixel perimeter), is a value from zero to one, with one representing a perfect circle.

Porous particles are described, for example, in U.S. patent application Ser. No. 10/637,130, filed on Aug. 8, 2003, and entitled "Embolization", which is incorporated herein by reference.

In general, various methods can be used to prepare particle 10. In some embodiments, particle 10 is formed using a drop generator.

Figure 2A:
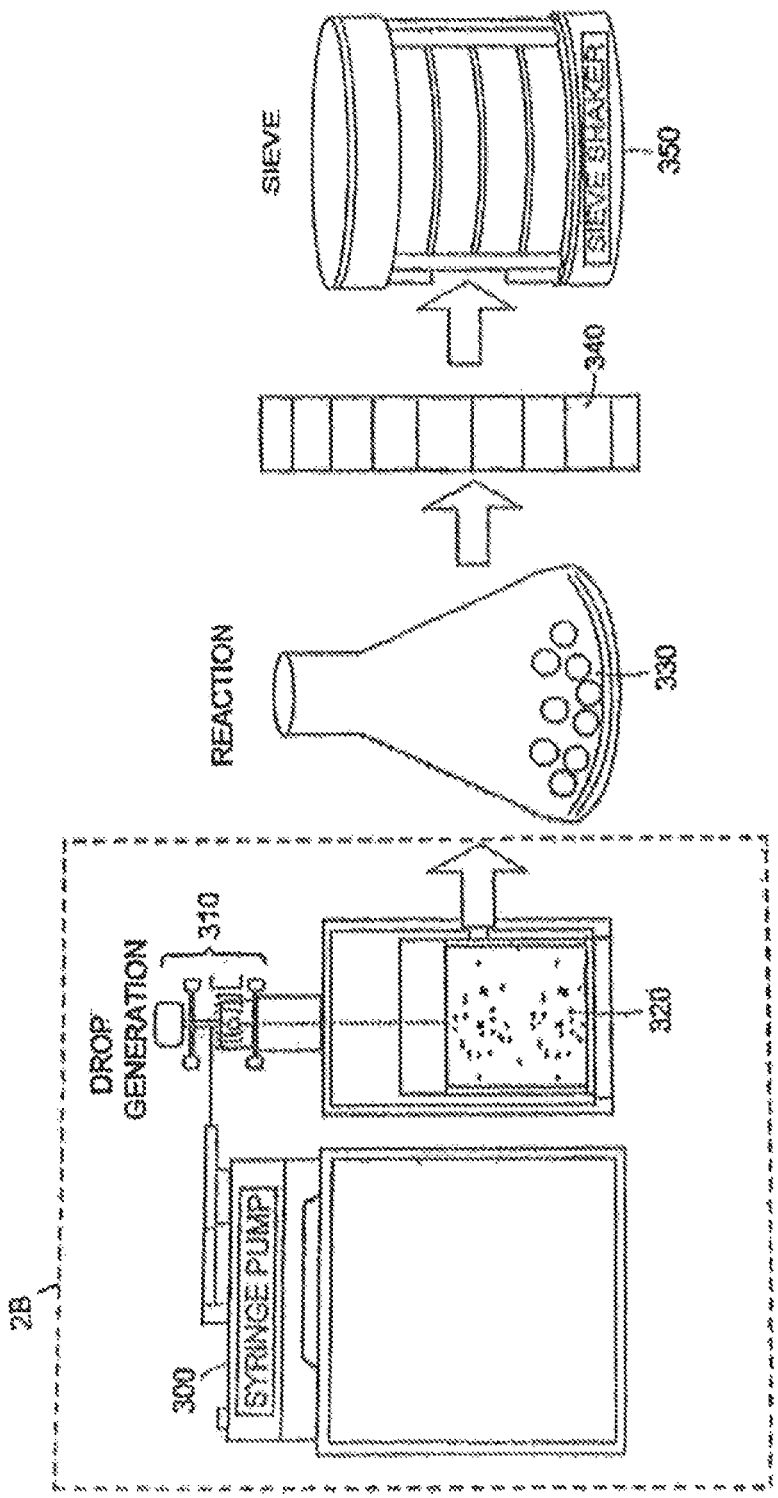
FIG. 2A is a schematic of an embodiment of a system for manufacturing particles.
Figure 2B:
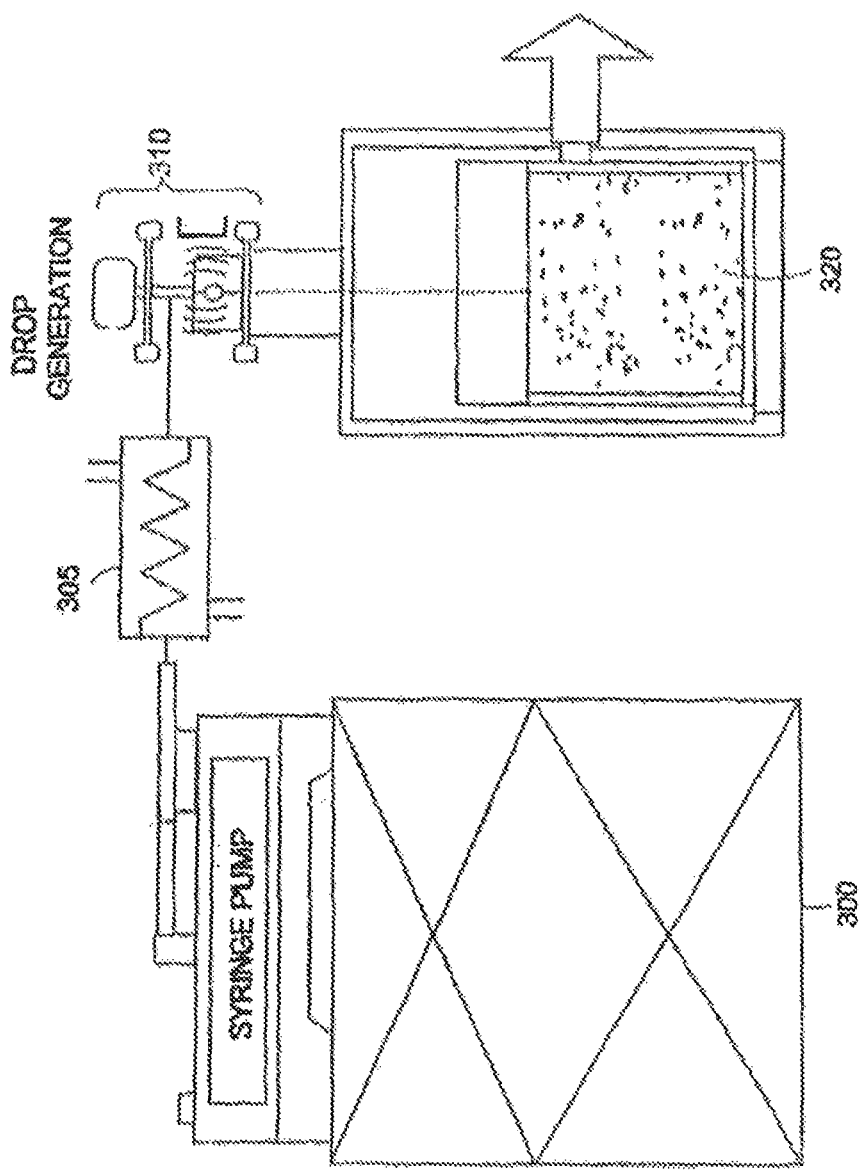
FIG. 2B is an enlarged schematic of region 2B in FIG. 2A.

FIG. 2A shows an embodiment of a system for producing particle 10. The system includes a flow controller 300, a drop generator 310, a gelling vessel 320, a reactor vessel 330, a gel dissolution chamber 340 and a filter 350. As shown in FIG. 2B, flow controller 300 delivers a solution that contains matrix material 12 (e.g., one or more polymers) and a gelling precursor (e.g., alginate) to a viscosity controller 305, which heats the solution to reduce viscosity prior to delivery to drop generator 310. The solution passes through an orifice in a nozzle in drop generator 310, forming drops of the solution. The drops are then directed into gelling vessel 320, where the drops contact a gelling agent (e.g., calcium chloride) that converts the gelling precursor from a solution form into a gel form, stabilizing the drops. The gel-stabilized drops are transferred from gelling vessel 320 to reactor vessel 330, where the polymer in the gel-stabilized drops is reacted (e.g., cross-linked), forming precursor particles. The precursor particles are transferred to gel dissolution chamber 340, where the gelling precursor (which was converted to a gel) is removed. The particles are then filtered in filter 350 to remove debris, and are sterilized and packaged as an embolic composition including the particles. Methods of making particles are described, for example, in U.S. patent application Ser. No. 10/637,130, filed on Aug. 8, 2003, and entitled "Embolization", which is incorporated herein by reference.

In some embodiments in which a drop generator is used in the preparation of particle 10, surface preferential material 14 is included in the solution delivered by the drop generator, and the solution is processed as described above to form particle 10. In certain embodiments in which a drop generator is used in the preparation of particle 10, surface preferential material 14 is included in the gelling vessel so that surface preferential material 14 is incorporated into the drop when the drop contacts the gelling agent. Combinations of these methods can be used.

In some embodiments, surface preferential material 14 is added to particle 10 in a separate operation. For example, surface preferential material 14 can be applied to the surface of particle 10 by compounding surface preferential material 14 with one or more of the coating materials (described below) and then applying the compounded coating material to the surface of particle 10. In certain embodiments, surface preferential material 14 can be placed in particle 10 (e.g., in one or more pores 16 or cavities of particle 10). In embodiments in which surface preferential material 14 is in liquid form prior to being incorporated into particle 10, surface preferential material 14 can be incorporated into particle 10 by, for example, absorption. Combinations of these methods can be used. For example, in some embodiments, one surface preferential material can be incorporated into a cavity in a particle, while another surface preferential material (either the same as, or different from, the first surface preferential material) can be absorbed through the surface of the particle.

In general, when surface preferential material 14 is added to particle 10 (e.g., during preparation of particle 10 or in a separate operation), surface preferential material 14 migrates toward region S of particle 10, thus typically causing region S to include a greater weight percent of surface preferential material 14 than region I.

In some embodiments, multiple particles are combined with a carrier fluid (e.g., a saline solution, a contrast agent, or both) to form an embolic composition. Such embolic compositions can be delivered to various sites in the body, including, for example, sites having cancerous lesions, such as the breast, prostate, lung, thyroid, or ovaries. The embolic compositions can be used in, for example, neural, pulmonary, and/or AAA (abdominal aortic aneurysm) applications. The compositions can be used in the treatment of, for example, fibroids, tumors, internal bleeding, arteriovenous malformations (AVMs), and/or hypervascular tumors. The compositions can be used as, for example, fillers for aneurysm sacs, AAA sac (Type II endoleaks), endoleak sealants, arterial sealants, and/or puncture sealants, and/or can be used to provide occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted. In some embodiments, a composition containing the particles can be used to prophylactically treat a condition.

The magnitude of a dose of an embolic composition can vary based on the nature, location and severity of the condition to be treated, as well as the route of administration. A physician treating the condition, disease or disorder can determine an effective amount of embolic composition. An effective amount of embolic composition refers to the amount sufficient to result in amelioration of symptoms or a prolongation of survival of the subject. The embolic compositions can be administered as pharmaceutically acceptable compositions to a subject in any therapeutically acceptable dosage, including those administered to a subject intravenously, subcutaneously, percutaneously, intratrachealy, intramuscularly, intramucosaly, intracutaneously, intra-articularly, orally or parenterally.

An embolic composition can include a mixture of particles (e.g., particles that include different types of therapeutic agents, particles that include different types of surface preferential materials), or can include particles that are all of the same type. In some embodiments, an embolic composition can be prepared with a calibrated concentration of particles for ease of delivery by a physician. A physician can select an embolic composition of a particular concentration based on, for example, the type of embolization procedure to be performed. In certain embodiments, a physician can use an embolic composition with a relatively high concentration of particles during one part of an embolization procedure, and an embolic composition with a relatively low concentration of particles during another part of the embolization procedure.

Suspensions of particles in saline solution can be prepared to remain stable (e.g., to remain suspended in solution and not settle and/or float) over a desired period of time. A suspension of particles can be stable, for example, for from about one minute to about 20 minutes (e.g. from about one minute to about ten minutes, from about two minutes to about seven minutes, from about three minutes to about six minutes).

In some embodiments, particles can be suspended in a physiological solution by matching the density of the solution to the density of the particles. In certain embodiments, the particles and/or the physiological solution can have a density of from about one gram per cubic centimeter to about 1.5 grams per cubic centimeter (e.g., from about 1.2 grams per cubic centimeter to about 1.4 grams per cubic centimeter, from about 1.2 grams per cubic centimeter to about 1.3 grams per cubic centimeter).

In some embodiments, the carrier fluid of an embolic composition can include a surfactant. The surfactant can help the particles to mix evenly in the carrier fluid and/or can decrease the likelihood of the occlusion of a delivery device (e.g., a catheter) by the particles. In some embodiments, the surfactant can enhance delivery of the embolic composition (e.g., by enhancing the wetting properties of the particles and facilitating the passage of the particles through a delivery device). In certain embodiments, the surfactant can decrease the occurrence of air entrapment by the particles in a composition (e.g., by porous particles in a composition). Examples of liquid surfactants include Tween® 80 (available from Sigma-Aldrich) and Cremophor EL® (available from Sigma-Aldrich). An example of a powder surfactant is Pluronic® F127 NF (available from BASF). In certain embodiments, an embolic composition can include from about 0.05 percent by weight to about one percent by weight (e.g., about 0.1 percent by weight, about 0.5 percent by weight) of a surfactant. A surfactant can be added to the carrier fluid prior to mixing with the particles and/or can be added to the particles prior to mixing with the carrier fluid.

Figure 3A:
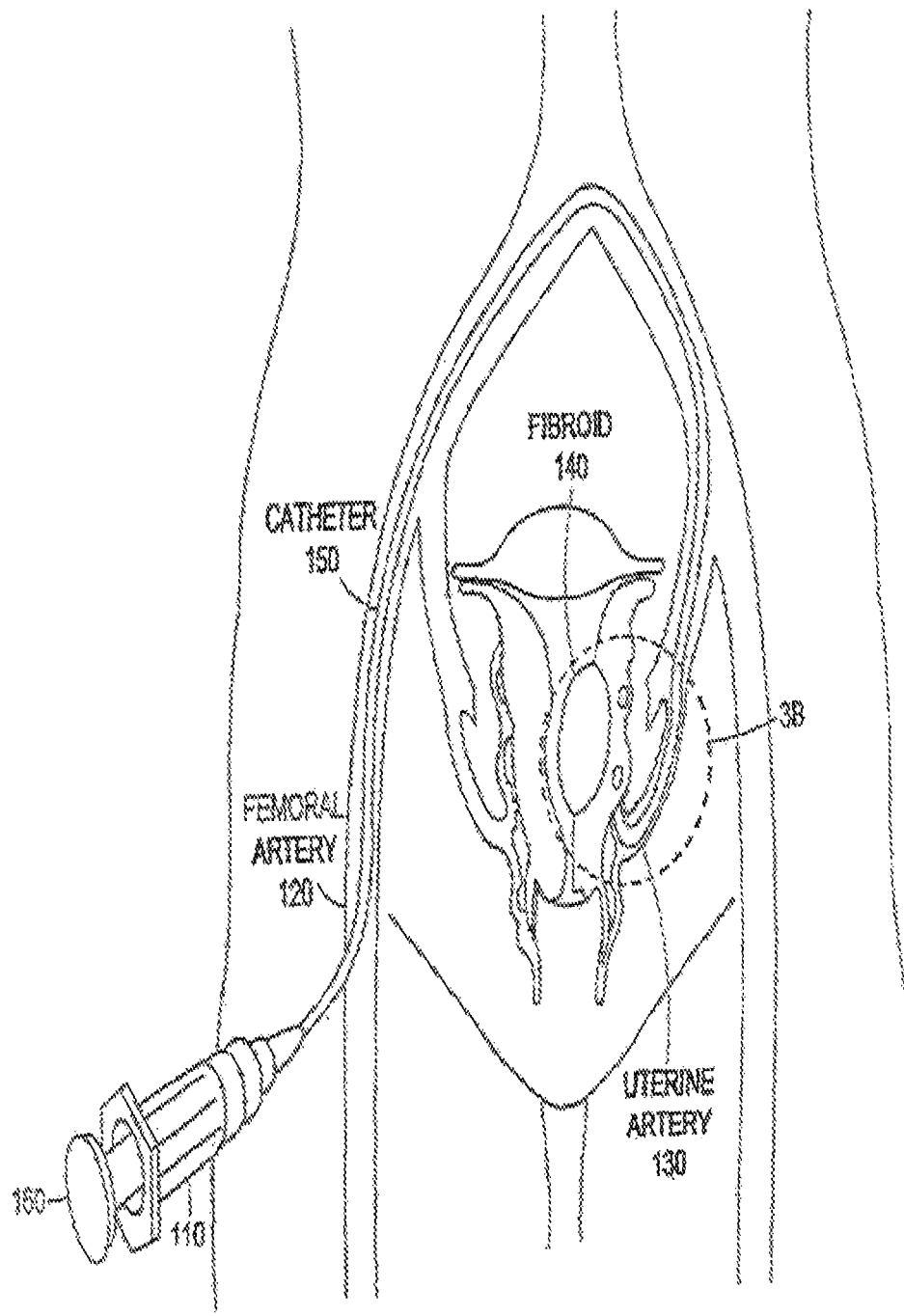
FIG. 3A is a schematic illustrating an embodiment of injection of an embolic composition including embolic particles into a vessel.
Figure 3B:
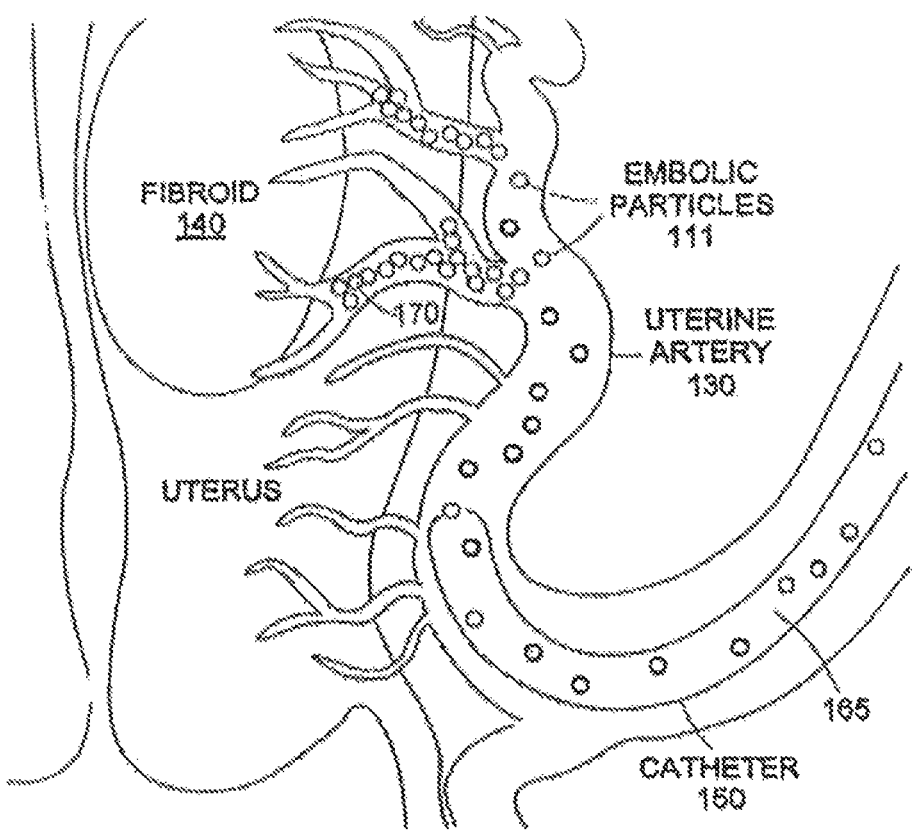
FIG. 3B is a greatly enlarged view of region 3B in FIG. 3A.

In FIGS. 3A and 3B, an embolic composition, including embolic particles 111 and a carrier fluid, is injected into a vessel through an instrument such as a catheter 150. Catheter 150 is connected to a syringe barrel 110 with a plunger 160. Catheter 150 is inserted, for example, into a femoral artery 120 of a subject. Catheter 150 delivers the embolic composition to, for example, occlude a uterine artery 130 leading to a fibroid 140. Fibroid 140 is located in the uterus of a female subject. The embolic composition is initially loaded into syringe 110. Plunger 160 of syringe 110 is then compressed to deliver the embolic composition through catheter 150 into a lumen 165 of uterine artery 130.

FIG. 3B, which is an enlarged view of section 3B of FIG. 3A, shows a uterine artery 130 that is subdivided into smaller uterine vessels 170 (e.g., having a diameter of about two millimeters or less) which feed fibroid 140. The embolic particles 111 in the embolic composition partially or totally fill the lumen of uterine artery 130, either partially or completely occluding the lumen of the uterine artery 130 that feeds uterine fibroid 140.

In some embodiments, among the particles delivered to a subject in an embolic composition, the majority (e.g., about 50 percent or more, about 60 percent or more, about 70 percent or more, about 80 percent or more, about 90 percent or more) of the particles have a diameter of about 3,000 microns or less (e.g., about 2,500 microns or less; about 2,000 microns or less; about 1,500 microns or less; about 1,200 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,200 microns or more; about 1,500 microns or more; about 2,000 microns or more; about 2,500 microns or more).

In certain embodiments, the particles delivered to a subject in an embolic composition have an arithmetic mean diameter of about 3,000 microns or less (e.g., about 2,500 microns or less; about 2,000 microns or less; about 1,500 microns or less; about 1,200 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,200 microns or more; about 1,500 microns or more; about 2,000 microns or more; about 2,500 microns or more). Exemplary ranges for the arithmetic mean diameter of particles delivered to a subject include from about 100 microns to about 500 microns; from about 100 microns to about 300 microns; from about 300 microns to about 500 microns; from about 500 microns to about 700 microns; and from about 900 microns to about 1,200 microns. In general, the particles delivered to a subject in an embolic composition have an arithmetic mean diameter in approximately the middle of the range of the diameters of the individual particles, and a variance of about 20 percent or less (e.g. about 15 percent or less, about ten percent or less).

In some embodiments, the arithmetic mean diameter of the particles delivered to a subject in an embolic composition can vary depending upon the particular condition to be treated. As an example, in embodiments in which the particles in an embolic composition are used to treat a liver tumor, the particles delivered to the subject can have an arithmetic mean diameter of about 500 microns or less (e.g., from about 100 microns to about 300 microns; from about 300 microns to about 500 microns). As another example, in embodiments in which the particles in an embolic composition are used to treat a uterine fibroid, the particles delivered to the subject in an embolic composition can have an arithmetic mean diameter of about 1,200 microns or less (e.g., from about 500 microns to about 700 microns; from about 700 microns to about 900 microns; from about 900 microns to about 1,200 microns).

The arithmetic mean diameter of a group of particles can be determined using a Beckman Coulter RapidVUE Image Analyzer version 2.06 (Beckman Coulter, Miami, Fla.), described above. The arithmetic mean diameter of a group of particles (e.g., in a composition) can be determined by dividing the sum of the diameters of all of the particles in the group by the number of particles in the group.

While certain embodiments have been described, the invention is not so limited.

As an example, in some embodiments a particle can be coated (e.g., with a bioabsorbable material). For example, a particle can include a polyvinyl alcohol matrix material, a surface preferential material that includes segmented polyurethane/DABs, polyethylene tetramethylene oxide, and a fraction of BA-L™, and a sodium alginate coating. The coating can contain, for example, one or more therapeutic agents, or can be substantially free of therapeutic agents. In certain embodiments, a particle can be coated to include a high concentration of one or more therapeutic agents that can alternatively or additionally be loaded into surface preferential material 14 and/or matrix material 12 of particle 10. The coating can release an initial dosage of therapeutic agent after which the body of the particle (e.g., region I and region S) can provide a burst release of therapeutic agent. The therapeutic agent in the coating can be the same as or different from the therapeutic agent in the body, region S, and/or region I of the particle. The therapeutic agent in the coating can be applied, for example, by exposing the particle to a high concentration solution of the therapeutic agent. Coatings are described, for example, in U.S. patent application Ser. No. 10/615,276, filed on Jul. 8, 2003, and entitled "Agent Delivery Particle", which is incorporated herein by reference.

In some embodiments, the coating can be, for example, a degradable and/or bioabsorbable polymer which erodes when the particle is administered. The coating can assist in controlling the rate at which therapeutic agent is released from the particle (e.g., from the surface preferential material). For example, the coating can be in the form of a porous membrane. The coating can delay an initial burst of therapeutic agent release. The coating can be applied by dipping or spraying the particle. The erodible polymer can be a polysaccharide (such as an alginate) or a polysaccharide derivative. In some embodiments, the coating can be an inorganic, ionic salt. Other erodible coatings include water soluble polymers (such as polyvinyl alcohol, e.g., that has not been cross-linked), biodegradable poly DL-lactide-poly ethylene glycol (PELA), hydrogels (e.g., polyacrylic acid, haluronic acid, gelatin, carboxymethyl cellulose), polyethylene glycols (PEG), chitosan, polyesters (e.g., polycaprolactones), and poly(lactic-co-glycolic) acids (e.g., poly(d-lactic-co-glycolic) acids). A polymer coating, e.g. an erodible coating, can be applied to the particle surface in embodiments in which a high concentration of therapeutic agent has not been applied to the particle surface. As an additional example, in some embodiments one or more particles is/are substantially non-spherical. In some embodiments, particles can be shaped (e.g., molded, compressed, punched, and/or agglomerated with other particles) at different points in the particle manufacturing process. In some embodiments (e.g., where matrix material 12 is a polymer such as a polyvinyl alcohol, and the gelling precursor is sodium alginate), after contacting the particles with the gelling agent but before cross-linking, the particles can be physically deformed into a specific shape and/or size. After shaping, the polymer matrix material 12 (e.g., polyvinyl alcohol) can be cross-linked, optionally followed by substantial removal of the gelling precursor (e.g., alginate). While substantially spherical particles are preferred, non-spherical particles can be manufactured and formed by controlling, for example, drop formation conditions. In some embodiments, nonspherical particles can be formed by post-processing the particles (e.g., by cutting or dicing into other shapes). Particle shaping is described, for example, in Baldwin et al., copending U.S. Published Patent Application No. US 2003/0203985 A1, which is incorporated herein by reference.

As a further example, in some embodiments the particles can be used for tissue bulking. As an example, the particles can be placed (e.g., injected) into tissue adjacent to a body passageway. The particles can narrow the passageway, thereby providing bulk and allowing the tissue to constrict the passageway more easily. The particles can be placed in the tissue according to a number of different methods, for example, percutaneously, laparoscopically, and/or through a catheter. In certain embodiments, a cavity can be formed in the tissue, and the particles can be placed in the cavity. Particle tissue bulking can be used to treat, for example, intrinsic sphincteric deficiency (ISD), vesicoureteral reflux, gastroesophageal reflux disease (GERD), and/or vocal cord paralysis (e.g., to restore glottic competence in cases of paralytic dysphonia). In some embodiments, particle tissue bulking can be used to treat urinary incontinence and/or fecal incontinence. The particles can be used as a graft material or a filler to fill and/or to smooth out soft tissue defects, such as for reconstructive or cosmetic applications (e.g., surgery). Examples of soft tissue defect applications include cleft lips, scars (e.g., depressed scars from chicken pox or acne scars), indentations resulting from liposuction, wrinkles (e.g., *glabella* frown wrinkles), and soft tissue augmentation of thin lips. Tissue bulking is described, for example, in Bourne et al., copending U.S. Published patent application No. US 2003/0233150 A1, which is incorporated herein by reference.

As another example, the particles can include other materials. For example, the particles can include (e.g., encapsulate) diagnostic agent(s) such as a radiopaque material, an MRI-visible material, a ferromagnetic material, and/or an ultrasound contrast agent. In some embodiments, surface preferential material 14 can include one or more of these diagnostic agents. Diagnostic agents are described, for example, in U.S. patent application Ser. No. 10/651,475, filed on Aug. 29, 2003, and entitled "Embolization", which is incorporated herein by reference.

As another example, in some embodiments particle 10 does not include a therapeutic agent (e.g., a therapeutic agent is not bound to surface preferential material 14).

As a further example, in some embodiments a particle can be formed without pores (nonporous particle).

As another example, in some embodiments a particle can include multiple (e.g., two, three, four, five, six) different surface preferential materials.

As an additional example, in some embodiments, it can be desirable to reduce the surface tension of the mixture contained in gelling vessel 320 (e.g., when forming particles having a diameter of about 500 microns or less). This can be achieved, for example, by heating the mixture in gelling vessel 320 (e.g., to a temperature greater than room temperature, such as a temperature of about 30° C. or more), by bubbling a gas (e.g., air, nitrogen, argon, krypton, helium, neon) through the mixture contained in gelling vessel 320, by stirring (e.g., via a magnetic stirrer) the mixture contained in gelling vessel 320, by including a surfactant in the mixture containing the gelling agent, and/or by forming a mist containing the gelling agent above the mixture contained in gelling vessel 320 (e.g., to reduce the formation of tails and/or enhance the sphericity of the particles).

Other embodiments are in the claims.

What is claimed is:

1. A particle having an interior region and a surface region, a weight percent of a first polymer present in the interior region being less than a weight percent of the first polymer present at the surface region, the particle having a diameter of from about ten microns to about 3,000 microns, wherein the first polymer has the formula D-B-[O-(AO)$_n$-B]$_m$-D, in which O is a first oligomeric segment, B is a first coupling segment, A is a second coupling segment, D is a polyfluoro oligomeric group comprising $CF_3(CF_2)_pCH_2CH_2$, m is from one to 20, and n is from zero to 20, and p is from two to 20.

2. The particle of claim 1, wherein the interior region is substantially devoid of the first polymer.

3. The particle of claim 1, wherein the interior region comprises at most about 50 weight percent of the first polymer.

4. The particle of claim 3, wherein the particle comprises from about 0.1 weight percent to about 90 weight percent of the first polymer.

5. The particle of claim 1, wherein the interior region comprises at least about 0.1 weight percent of the first polymer.

6. The particle of claim 1, wherein the surface region comprises at least about 0.1 weight percent of the first polymer.

7. The particle of claim 6, wherein the particle comprises from about 0.1 weight percent to about 90 weight percent of the first polymer.

8. The particle of claim 1, wherein the surface region comprises at most about 100 weight percent of the first polymer.

9. The particle of claim 1, wherein the difference between the weight percent of the first polymer in the interior region and the weight percent of the first polymer at the surface region is at least about 30 weight percent.

10. The particle of claim 1, wherein the particle has a diameter of at least about 100 microns.

11. The particle of claim 1, wherein the particle has a diameter of at most about 2,500 microns.

12. The particle of claim 1, wherein the first polymer comprises a halogenated polymer.

13. The particle of claim 1, wherein the first polymer comprises a fluorinated polymer.

14. The particle of claim 1, wherein the first polymer comprises a backbone and side groups that are more polar than the backbone.

15. The particle of claim 1, wherein the first polymer has a molecular weight of from about 500 to about 15,000.

16. The particle of claim 1, wherein the first polymer is linear.

17. The particle of claim 1, wherein O comprises a member selected from the group consisting of polyurethanes, polyureas, polyamides, polyalkylene oxides, polycarbonates, polyesters, polylactones, polysilicones, polyethersulfones, polyolefins, polyvinyls, polypeptide polysaccharides, and ether and amine linked segments thereof.

18. The particle of claim 1, wherein A comprises a member selected from the group consisting of diamines, diisocyanates, disulfonic acids, dicarboxylic acids, diacid chlorides, and dialdehydes.

19. The particle of claim 1, wherein B comprises a member selected from the group consisting of diamines, diisocyanates, disulfonic acids, dicarboxylic acids, diacid chlorides, and dialdehydes.

20. The particle of claim 19, wherein B further comprises a functional group selected from the group consisting of esters, carboxylic acid salts, sulfonic acid salts, phosphonic acid salts, thiols, vinyls, and secondary amines.

21. The particle of claim 1, wherein the particle further comprises a therapeutic agent.

22. The particle of claim 1, wherein the particle further comprises a second polymer.

23. The particle of claim 22, wherein the second polymer comprises a member selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids, and combinations thereof.

24. The particle of claim 22, wherein the particle further comprises a therapeutic agent.

25. The particle of claim 24, wherein the therapeutic agent is bound to the first polymer.

26. The particle of claim 1, wherein the particle further comprises a polysaccharide.

27. The particle of claim 1, wherein the particle is spherical.

28. The particle of claim 1, wherein the particle further comprises a coating disposed over the surface region.

29. The particle of claim 28, wherein the coating is bioabsorbable.

30. The particle of claim 1, wherein the particle comprises from about 0.25 weight percent to about 50 weight percent of the first polymer.

31. The particle of claim 1, wherein the particle comprises from about 15 weight percent to about 35 weight percent of the first polymer.

32. The particle of claim 1, wherein the interior region has a density of large pores and the surface region has a density of large pores, and the density of large pores of the interior region is greater than the density of large pores at the surface region.

33. A particle having an interior region and a surface region, a weight percent of a first polymer present in the interior region being less than a weight percent of the first polymer present at the surface region, the particle having a diameter of from about ten microns to about 3,000 microns, wherein the first polymer has the formula D-B-[O-(AO)$_n$-B]$_m$-D, in which O is a first oligomeric segment, B is a first coupling segment, A is a second coupling segment, D is a polyfluoro oligomeric group comprising $CF_3(CF_2)_m(CH_2CH_2)_q$, m is from one to 20, and n is from zero to 20, and q is from one to ten.

* * * * *